US008654185B2

(12) United States Patent
Ono

(10) Patent No.: US 8,654,185 B2
(45) Date of Patent: Feb. 18, 2014

(54) FLUORESCENCE OBSERVATION APPARATUS

(71) Applicant: Olympus Corporation, Tokyo (JP)

(72) Inventor: Fumiko Ono, Tokyo (JP)

(73) Assignee: Olympus Corporation, Tokyo (JP)

(*) Notice: Subject to any disclaimer, the term of this patent is extended or adjusted under 35 U.S.C. 154(b) by 0 days.

(21) Appl. No.: 13/726,987

(22) Filed: Dec. 26, 2012

(65) Prior Publication Data
US 2013/0113907 A1 May 9, 2013

Related U.S. Application Data

(63) Continuation of application No. PCT/JP2011/064901, filed on Jun. 29, 2011.

(30) Foreign Application Priority Data

Jul. 6, 2010 (JP) ................................ 2010-153877

(51) Int. Cl.
A61B 1/04 (2006.01)
A61B 6/00 (2006.01)

(52) U.S. Cl.
USPC ............................................ 348/68; 600/476

(58) Field of Classification Search
USPC ............................................ 348/68; 600/476
See application file for complete search history.

(56) References Cited

U.S. PATENT DOCUMENTS

2010/0204544 A1* 8/2010 Takei .............................. 600/109

FOREIGN PATENT DOCUMENTS

JP 62-247232 10/1987
JP 9-294706 11/1997
JP 2008-229025 A 10/2008

OTHER PUBLICATIONS

International Search Report PCT/JP2011/064901 dated Aug. 2, 2011.

* cited by examiner

Primary Examiner — Dave Czekaj
Assistant Examiner — Tsion B Owens
(74) Attorney, Agent, or Firm — Scully, Scott, Murphy & Presser, P.C.

(57) ABSTRACT

Provided is a fluorescence observation apparatus including an illumination unit that irradiates an object with illumination light and excitation light; a fluorescence-image acquisition unit that captures an image of the fluorescence generated by the object, thereby acquiring a fluorescence image; a return-light-image acquisition unit that captures an image of the return light returning from the object, thereby acquiring a return-light image; a light-distribution-characteristics-information storage unit that stores information with regard to the light distribution characteristics of optical systems; an image correcting unit that corrects at least one of the fluorescence image and the return-light image using the information so that the light distribution characteristics contained in the fluorescence image and the return-light image are made equal to each other; and an image normalizing unit that normalizes the fluorescence image on the basis of the return-light image, using the corrected fluorescence image and return-light image.

5 Claims, 7 Drawing Sheets

FLUORESCENCE OBSERVATION APPARATUS

CROSS REFERENCE TO RELATED APPLICATIONS

This is a continuation of International Application PCT/JP2011/064901, with an international filing date of Jun. 29, 2011, which is hereby incorporated by reference herein in its entirety.

BACKGROUND OF THE INVENTION

1. Field of the Invention

The present invention relates to fluorescence observation apparatuses.

2. Description of Related Art

A known fluorescence measuring apparatus in the related art performs normalization by irradiating an observation target with excitation light, detecting fluorescence generated by the observation target as well as reflected light of the excitation light reflected at the surface of the observation target, and dividing the fluorescence intensity by the detected reflected light intensity (for example, see Japanese Unexamined Patent Application, Publication No. S62-247232).

With this fluorescence measuring apparatus, even if the generated fluorescence varies according to changes in the distance and angle between an excitation-light emitting end and the observation target, it is possible to normalize the fluorescence and reduce the influence of the distance and angle, thereby improving the quantitativeness of the fluorescence observation.

BRIEF SUMMARY OF THE INVENTION

An aspect of the present invention provides a fluorescence observation apparatus including an illumination unit that irradiates an object with illumination light and excitation light; a fluorescence-image acquisition unit that captures an image of fluorescence generated by the object due to the object being irradiated with the excitation light from the illumination unit, thereby acquiring a fluorescence image; a return-light-image acquisition unit that captures an image of return light returning from the object due to the object being irradiated with the illumination light from the illumination unit, thereby acquiring a return-light image; a light-distribution-characteristics-information storage unit that stores information with regard to the light distribution characteristics of optical systems provided in the fluorescence-image acquisition unit and in the return-light-image acquisition unit; an image correcting unit that corrects at least one of the fluorescence image and the return-light image using the information with regard to the light distribution characteristics stored in the light-distribution-characteristics-information storage unit so that the light distribution characteristics contained in the fluorescence image and the return-light image are made equal to each other; and an image normalizing unit that normalizes the fluorescence image on the basis of the return-light image, each of the fluorescence image and the return-light image being corrected by the image correcting unit.

According to this aspect, the fluorescence-image acquisition unit captures an image of fluorescence generated by the object due to the object being irradiated with the excitation light from the illumination unit, thereby acquiring a fluorescence image, whereas the return-light-image acquisition unit captures an image of the return light returning from the object due to the object being irradiated with the illumination light from the illumination unit, thereby acquiring a return-light image. The fluorescence-image acquisition unit and the return-light-image acquisition unit are provided with optical systems having different light distribution characteristics, due to their different purposes, and the information with regard to the light distribution characteristics of these optical systems is stored in the light-distribution-characteristics-information storage unit.

Then, the image correcting unit corrects at least one of the fluorescence image and the return-light image using the information with regard to the light distribution characteristics stored in the light-distribution-characteristics-information storage unit so that the light distribution characteristics contained in the fluorescence image and the return-light image are made equal to each other.

In the above-described aspect, the light-distribution-characteristics-information storage unit may store, as the information with regard to the light distribution characteristics of the optical systems, the light distribution characteristics of the optical systems provided in the fluorescence-image acquisition unit and in the return-light-image acquisition unit, and the image correcting unit may divide the fluorescence image by the light distribution characteristics of the optical system provided in the fluorescence-image acquisition unit and may divide the return-light image by the light distribution characteristics of the optical system provided in the return-light-image acquisition unit.

Furthermore, in the above-described aspect, the light-distribution-characteristics-information storage unit may store, as the information with regard to the light distribution characteristics of the optical systems, a light-distribution-characteristics ratio obtained by dividing the light distribution characteristics of the optical system provided in the fluorescence-image acquisition unit by the light distribution characteristics of the optical system provided in the return-light-image acquisition unit, and the image correcting unit may divide the fluorescence image by the light-distribution-characteristics ratio. Furthermore, in the above-described aspect, the light-distribution-characteristics-information storage unit may store, as the information with regard to the light distribution characteristics of the optical systems, a light-distribution-characteristics ratio obtained by dividing the light distribution characteristics of the optical system provided in the return-light-image acquisition unit by the light distribution characteristics of the optical system provided in the fluorescence-image acquisition unit, and the image correcting unit may divide the return-light image by the light-distribution-characteristics ratio.

Furthermore, another aspect of the present invention provides a fluorescence observation apparatus including an illumination unit that irradiates an object with illumination light and excitation light; a fluorescence-image acquisition unit that captures an image of fluorescence generated by the object due to the object being irradiated with the excitation light from the illumination unit, thereby acquiring a fluorescence image; a return-light-image acquisition unit that captures an image of return light returning from the object due to the object being irradiated with the illumination light from the illumination unit, thereby acquiring a return-light image; a light-distribution-characteristics-information storage unit that stores information with regard to the light distribution characteristics of optical systems provided in the fluorescence-image acquisition unit and in the return-light-image acquisition unit; an image normalizing unit that normalizes the fluorescence image acquired by the fluorescence-image acquisition unit on the basis of the return-light image acquired by the return-light-image acquisition unit; and an image correcting unit that corrects the fluorescence image normalized by the image normalizing unit using the information with regard to the light distribution characteristics stored in the light-distribution-characteristics-information storage unit so that the light distribution characteristics contained in the fluorescence image and the return-light image are made equal to each other.

BRIEF DESCRIPTION OF THE SEVERAL VIEWS OF THE DRAWINGS

FIG. 2 is a diagram showing example light distribution characteristics of focusing lenses provided in the fluorescence observation apparatus in FIG. 1, in which FIG. 2(a) shows the light distribution characteristics of a fluorescence focusing lens, and FIG. 2(b) shows the light distribution characteristics of a white light focusing lens.

DETAILED DESCRIPTION OF THE INVENTION

A fluorescence observation apparatus 1 according to an embodiment of the present invention will be described below with reference to the drawings.

Figure 1:
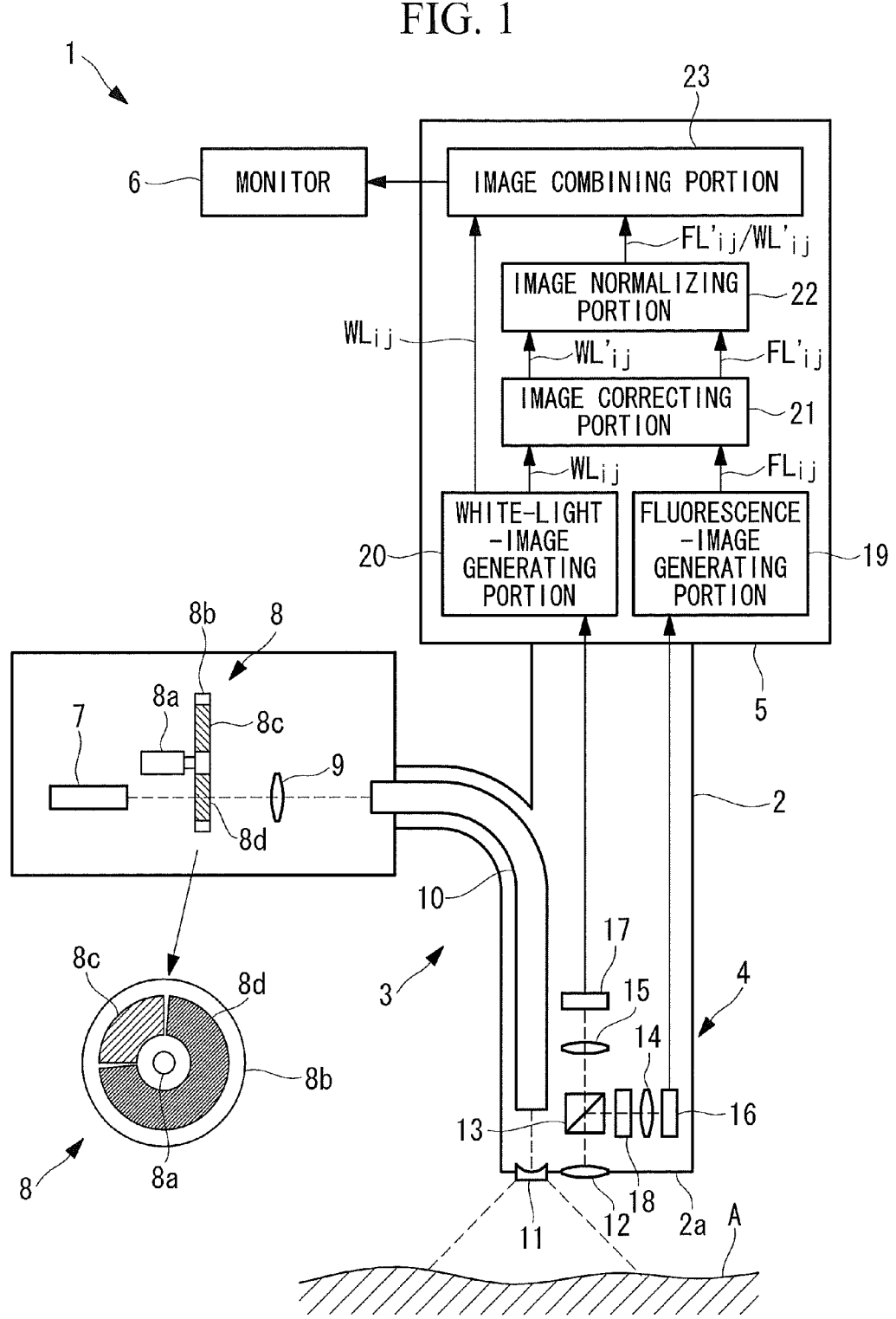
FIG. 1 is a diagram showing the overall configuration of a fluorescence observation apparatus according to an embodiment of the present invention.

As shown in FIG. 1, the fluorescence observation apparatus 1 according to this embodiment is an endoscope apparatus and includes an insertion unit 2 to be inserted into a body cavity; an illumination unit 3 that irradiates biological tissue (hereinbelow referred to as an "object") A disposed so as to face a distal end face 2a of the insertion unit 2 with white light (illumination light) and excitation light; an image acquisition unit 4 that acquires a fluorescence image signal and a white-light image signal from the object A; an image processing unit 5 that processes the image signals acquired by the image acquisition unit 4; and a monitor 6 that displays an image generated by the image processing unit 5.

The illumination unit 3 includes a xenon lamp 7, a filter 8, a coupling lens 9, a light guide fiber 10, and an illumination optical system 11. The filter 8 includes a white light filter 8c that allows light in a wavelength range of white light (for example, 400 nm to 650 nm) to pass therethrough and an excitation light filter 8d that allows light in a wavelength range of excitation light (for example, 650 nm to 750 nm) to pass therethrough. The white light filter 8c and the excitation light filter 8d are arranged circumferentially side-by-side on a turret 8b that is rotated by a motor 8a.

The coupling lens 9 focuses the white light and excitation light passing through the filter 8 and makes them incident on an end of the light guide fiber 10. The light guide fiber 10 is disposed over the whole length of the insertion unit 2, i.e., from the base end to the distal end, and guides the white light and the excitation light to the distal end face 2a of the insertion unit 2. The illumination optical system 11 spreads out the white light and excitation light guided by the light guide fiber 10 and emits the white light and excitation light to the object A.

The image acquisition unit 4 is disposed at the distal end of the insertion unit 2 and includes an objective lens 12 that collects the fluorescence generated by the object A and return light of the white light from the object; a dichroic mirror 13 that splits the light collected by the objective lens 12 into the fluorescence and the white light; focusing lenses 14 and 15 that focus the fluorescence and white light, respectively, split by the dichroic mirror 13; a fluorescence CCD (fluorescence-image acquisition unit) 16 that captures an image of the fluorescence focused by the focusing lens 14; and a white light CCD (return-light-image acquisition unit) 17 that captures an image of the white light focused by the focusing lens 15. In the diagram, reference numeral 18 represents an excitation-light cut filter that blocks the excitation light incident on the fluorescence CCD 16.

Figure 2:
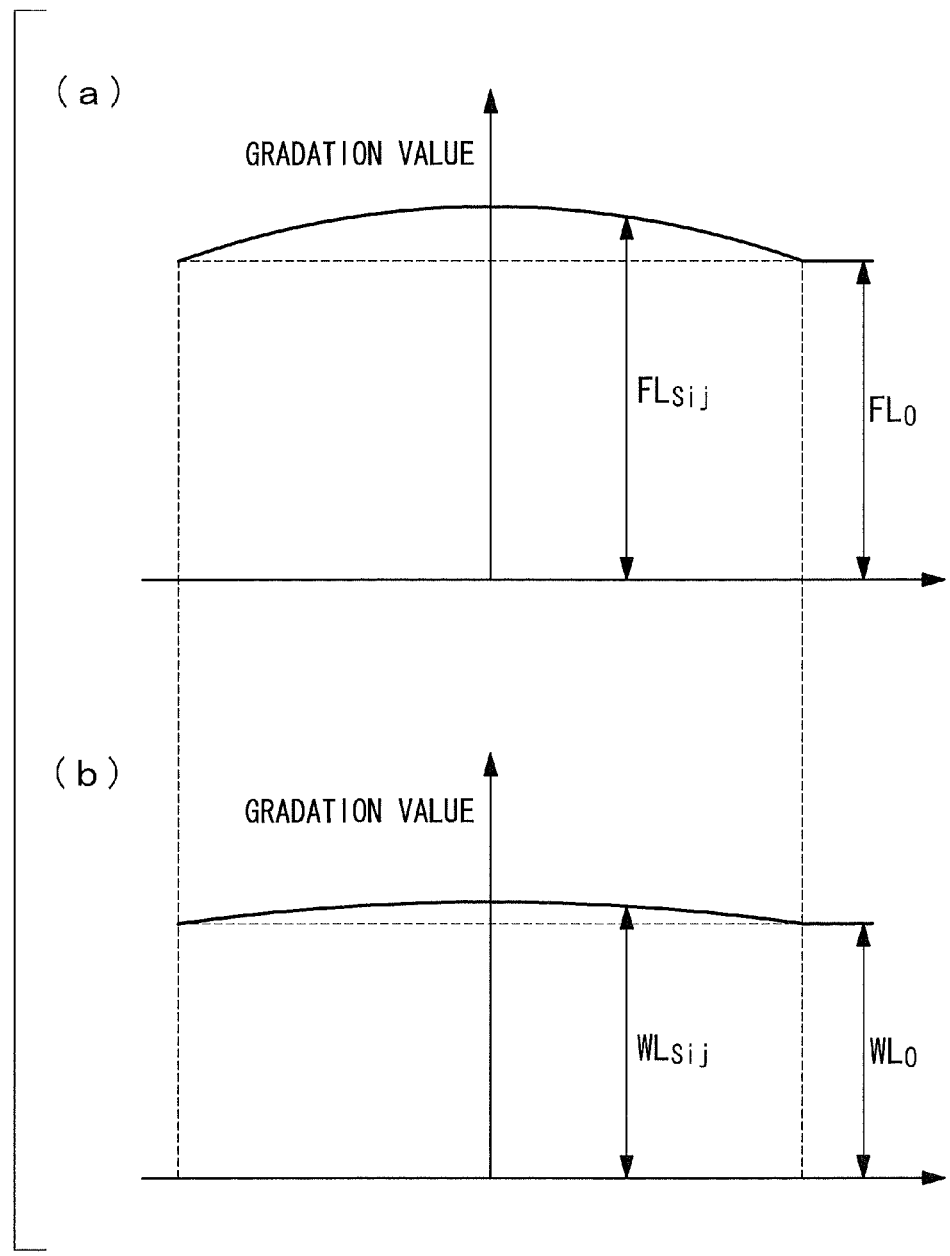

The focusing lens 14, which focuses faint fluorescence to acquire a bright fluorescence image, and the focusing lens 15, which focuses white light to acquire a sharp white-light image, have different light distribution characteristics due to their different purposes. The light distribution characteristics of the focusing lenses 14 and 15 are, for example, shown in FIG. 2.

FIGS. 2(a) and 2(b) show example light distribution characteristics. These light distribution characteristics are the gradation-value distributions on the same straight line on the fluorescence image and white-light image acquired by irradiating, with excitation light and white light, a reference sample that evenly contains fluorochrome and has optical properties similar to those of biological tissue.

FIG. 2(a) shows example light distribution characteristics of the focusing lens 14 along a straight line in an area irradiated with excitation light. The gradation value of the fluorescence at an end of the straight line is denoted by $FL_O$, and the gradation value of the fluorescence at an arbitrary position on the straight line on the reference sample is denoted by $FL_{Sij}$. Herein, subscripts i and j are natural numbers that indicate a pixel position in two orthogonal directions in the fluorescence image.

FIG. 2(b) shows example light distribution characteristics of the focusing lens 15, along a straight line in a white-light irradiation area. The gradation value of the fluorescence at an end of the straight line is denoted by $WL_O$, and the gradation value of the fluorescence at an arbitrary position on the straight line on the reference sample is denoted by $WL_{Sij}$. Herein, subscripts i and j are natural numbers that indicate a pixel position in two orthogonal directions in the white-light image.

The image processing unit 5 includes a fluorescence-image generating portion 19 that processes the fluorescence image signal acquired by the fluorescence CCD 16 and generates a fluorescence image; a white-light-image generating portion 20 that processes the white-light image signal acquired by the white light CCD 17 and generates a white-light image; an image correcting portion 21 that corrects the generated fluorescence image and white-light image; an image normalizing portion 22 that normalizes the fluorescence image by the white-light image, using the corrected fluorescence image and the corrected white-light image; and an image combining portion 23 that combines the normalized fluorescence image and the white-light image.

The image correcting portion 21 stores a correction coefficient for the fluorescence image and a correction coefficient for the white-light image. The correction coefficients are calculated as ratios $F_{ij}=FL_{Sij}/FL_O$ and $W_{ij}=WL_{Sij}/WL_O$, which are the light distribution characteristics $FL_{Sij}$ and $WL_{Sij}$ of the focusing lenses 14 and 15 divided by gradation values $FL_O$ and $WL_O$ at a representative common pixel position, when the reference sample is used.

The image correcting portion 21 calculates a corrected fluorescence image $FL'_{ij}$ and a corrected white-light image $WL'_{ij}$ by dividing a gradation value $FL_{ij}$ and a gradation value $WL_{ij}$ at each pixel position in the fluorescence image and white-light image obtained by irradiating the object A with the excitation light and the white light by the stored correction coefficients F and W.

The fluorescence image $FL'_{ij}$ and white-light image $WL'_{ij}$ corrected in the image correcting portion 21 are sent to the image normalizing portion 22, where the corrected fluorescence image $FL'_{ij}$ is divided by the corrected white-light image $WL'_{ij}$, and a normalized fluorescence image is acquired. The thus-acquired normalized fluorescence image is combined with the white-light image by the image combining unit and is output to the monitor 6.

The operation of the thus-configured fluorescence observation apparatus 1 according to this embodiment will be described below.

To observe the fluorescence of the object A using the fluorescence observation apparatus 1 according to this embodiment, illumination light generated by activating a xenon lamp is allowed to successively pass through the white light filter 8c and the excitation light filter 8d by operating the filter motor to rotate the turret.

Figure 3:
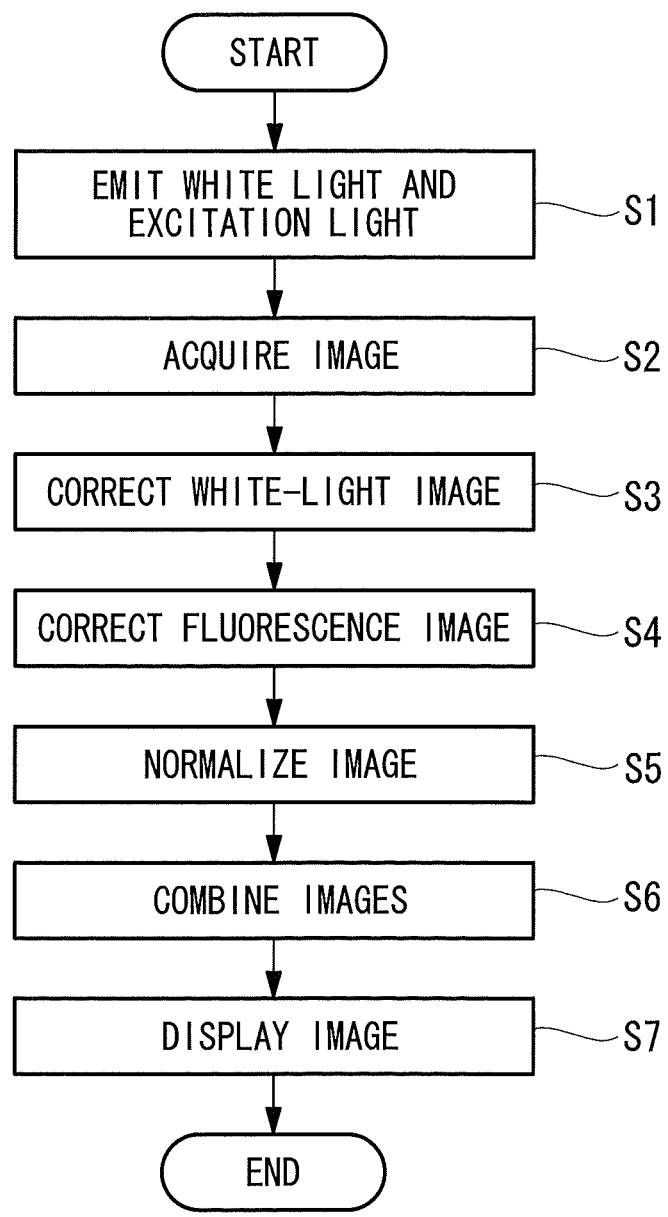
FIG. 3 is a flowchart showing a process of observing fluorescence from an object using the fluorescence observation apparatus in FIG. 1.

As shown in FIGS. 1 and 3, the white light passing through the white light filter 8c and the excitation light passing through the excitation light filter 8d are successively made incident on the end face of the light guide fiber 10 by the coupling lens, are guided to the distal end face 2a of the insertion unit 2, and are emitted to the surface of the object A by the illumination optical system 11 (Step S1). The white light emitted to the surface of the object A is reflected at the surface and is collected by the objective lens 12. Meanwhile, when the object A is irradiated with the excitation light, a fluorescent substance existing in the object A is excited, and fluorescence is generated. Of the generated fluorescence, a portion of the fluorescence emitted from the surface of the object A is collected by the objective lens 12.

The white light collected by the objective lens 12 passes through the dichroic mirror 13 and is focused by the focusing lens 15, and an image of the white light is captured by the white light CCD 17. Meanwhile, the fluorescence collected by the objective lens 12 is reflected by the dichroic mirror 13 and is focused by the focusing lens 14, and an image of the fluorescence is captured by the fluorescence CCD 16. In this way, the white-light image signal and the fluorescence image signal are acquired (step S2).

The white-light image signal and the fluorescence image signal are sent to the white-light-image generating portion 20 and fluorescence-image generating portion 19 of the image processing unit 5, respectively, where a white-light image $WL_{ij}$ and a fluorescence image $FL_{ij}$ are generated. Then, the generated white-light image $WL_{ij}$ and fluorescence image $FL_{ij}$ are sent to the image correcting portion 21, where a corrected white-light image $WL'_{ij}$ and a corrected fluorescence image $FL'_{ij}$ are acquired (steps S3 and S4).

The corrected white-light image $WL'_{ij}$ and fluorescence image $FL'_{ij}$ are sent to the image normalizing portion 22, where the corrected fluorescence image $FL'_{ij}$ is divided by the corrected white-light image $WL'_{ij}$. Thus, a normalized fluorescence image $FL'_{ij}/WL'_{ij}$ is acquired (step S5). The fluorescence image $FL'_{ij}/WL'_{ij}$ is then sent to the image combining portion 23, where it is combined with the white-light image $WL_{ij}$ (step S6) and is displayed on the monitor 6 (step S7).

As described above, the fluorescence observation apparatus 1 according to this embodiment corrects the fluorescence image and white-light image, which have been acquired by using the focusing lenses 14 and 15 having different light distribution characteristics, by dividing these images by the light distribution characteristics of the focusing lenses 14 and 15 used to acquire these images. Thus, there is an advantage in that it is possible to normalize the fluorescence image using the fluorescence image and white-light image that are less affected by the light distribution characteristics, whereby it is possible to observe the object A using a normalized fluorescence image having higher quantitativeness.

In this embodiment, the light distribution characteristics of the focusing lenses 14 and 15 are separately stored, the acquired fluorescence image and white-light image are corrected by the light distribution characteristics of the focusing lenses 14 and 15 used to acquire these images, and the corrected fluorescence image is normalized by the corrected white-light image. However, a method shown in FIGS. 4 and 5 may be employed instead.

Figure 4:
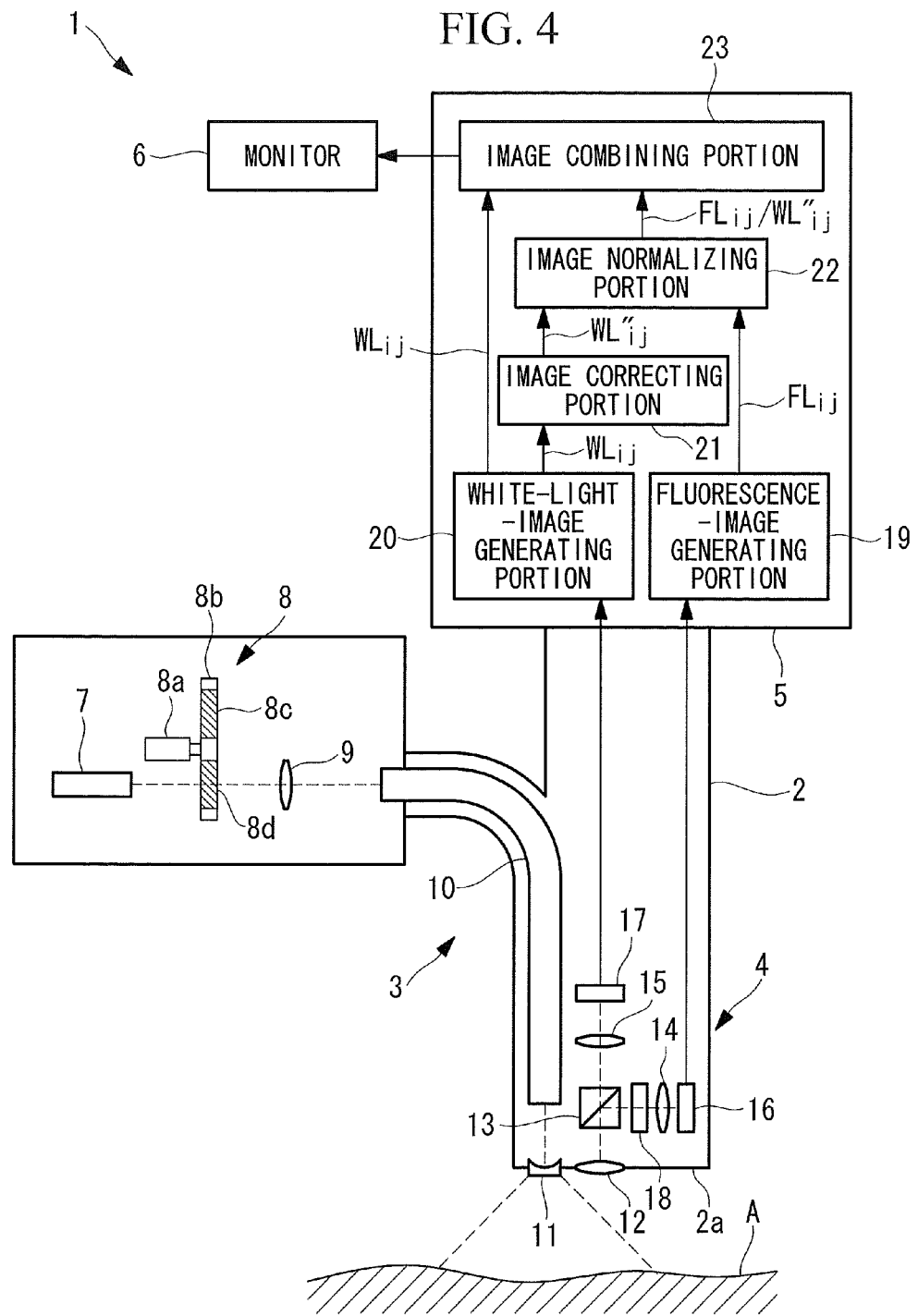
FIG. 4 is a diagram showing the overall configuration of a first modification of the fluorescence observation apparatus in FIG. 1.

More specifically, in an example shown in FIG. 4, the image correcting portion 21 stores correction coefficient W/F and divides the white-light image $WL_{ij}$ generated by the white-light-image generating portion 20 by the correction coefficients W/F, thus calculating the corrected white-light image $WL''_{ij}$. Then, the image normalizing portion 22 divides the fluorescence image $FL_{ij}$ generated by the fluorescence-image generating portion 19 by the corrected white-light image $WL''_{ij}$.

Figure 5:
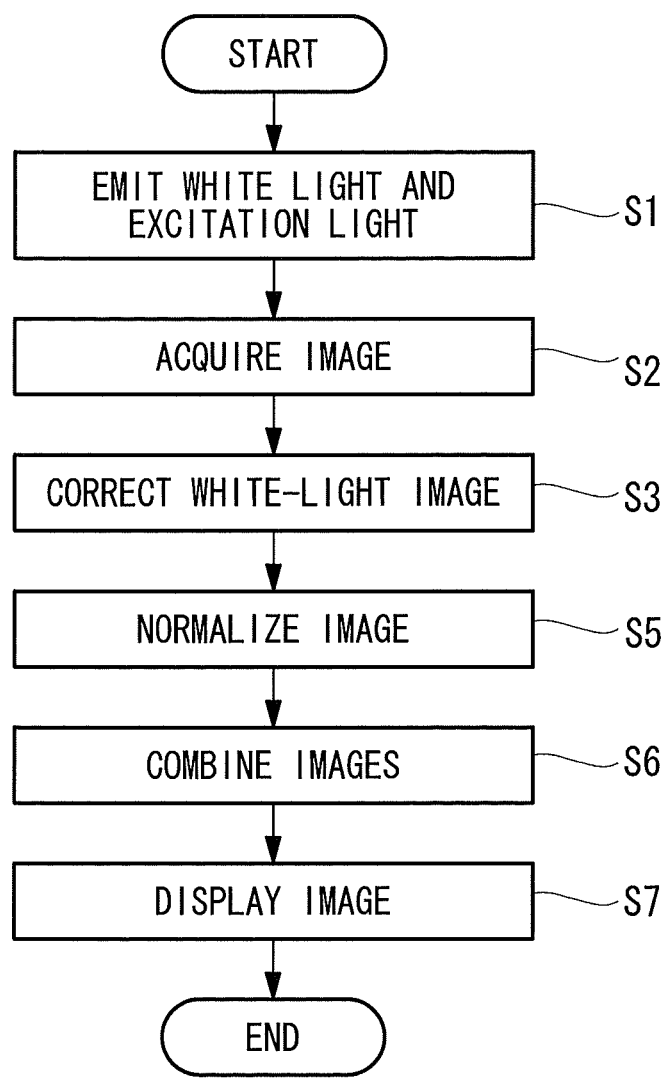
FIG. 5 is a flowchart showing a process of observing fluorescence from an object using the fluorescence observation apparatus in FIG. 4.

Thus, it is possible to acquire a normalized fluorescence image the same as that in FIG. 1. In this case, as shown in FIG. 5, a fluorescence-image correcting step S4 existing in the flowchart in FIG. 3 can be omitted, whereby it is possible to reduce the amount of calculation and increase the processing speed.

Conversely, it is also possible that the image correcting portion 21 stores correction coefficient F/W and corrects the fluorescence image by the correction coefficient, and the corrected fluorescence image is divided by the white-light image generated by the white-light-image generating portion 20.

Figure 6:
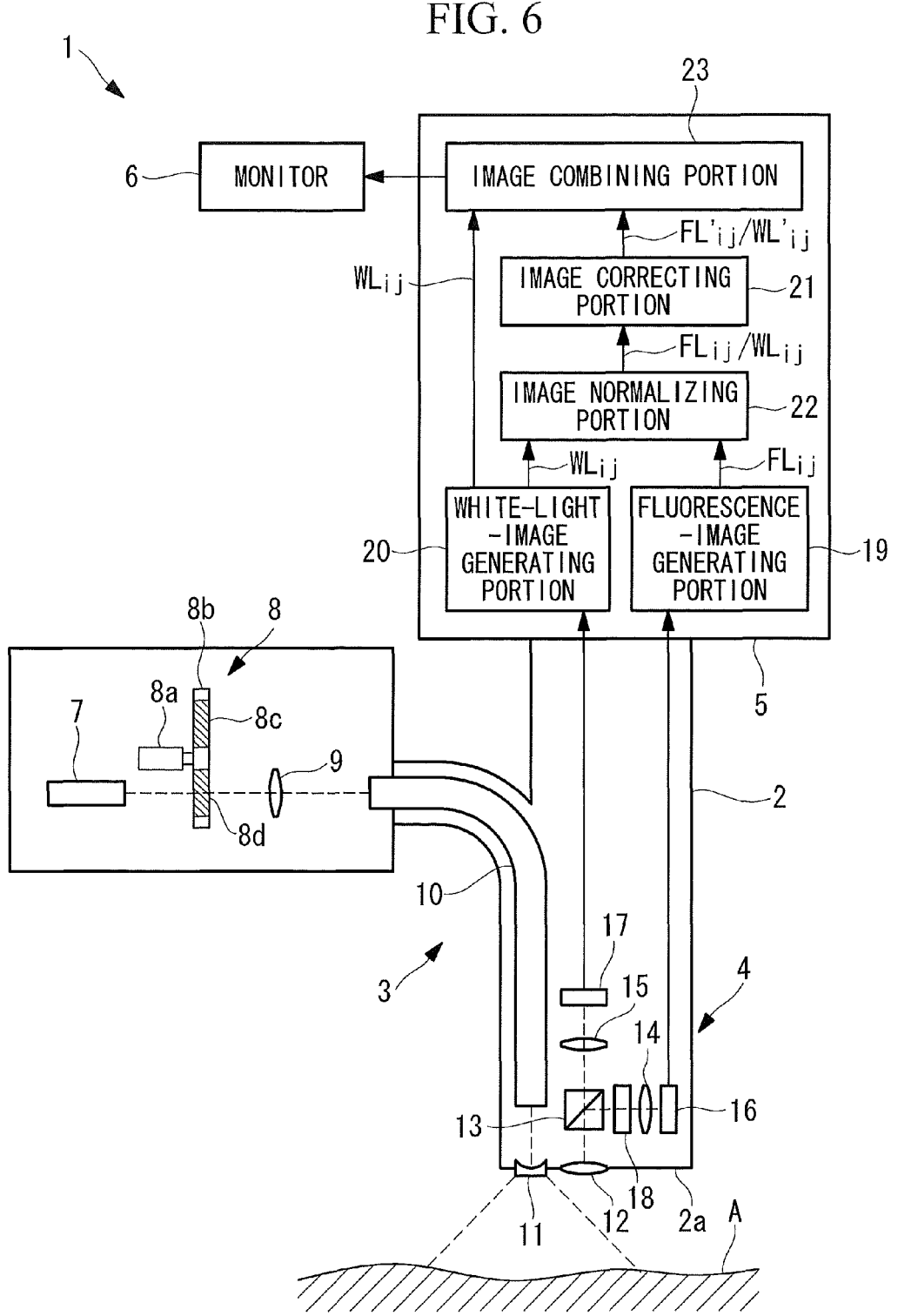
FIG. 6 is a diagram showing the overall configuration of a second modification of the fluorescence observation apparatus in FIG. 1.
Figure 7:
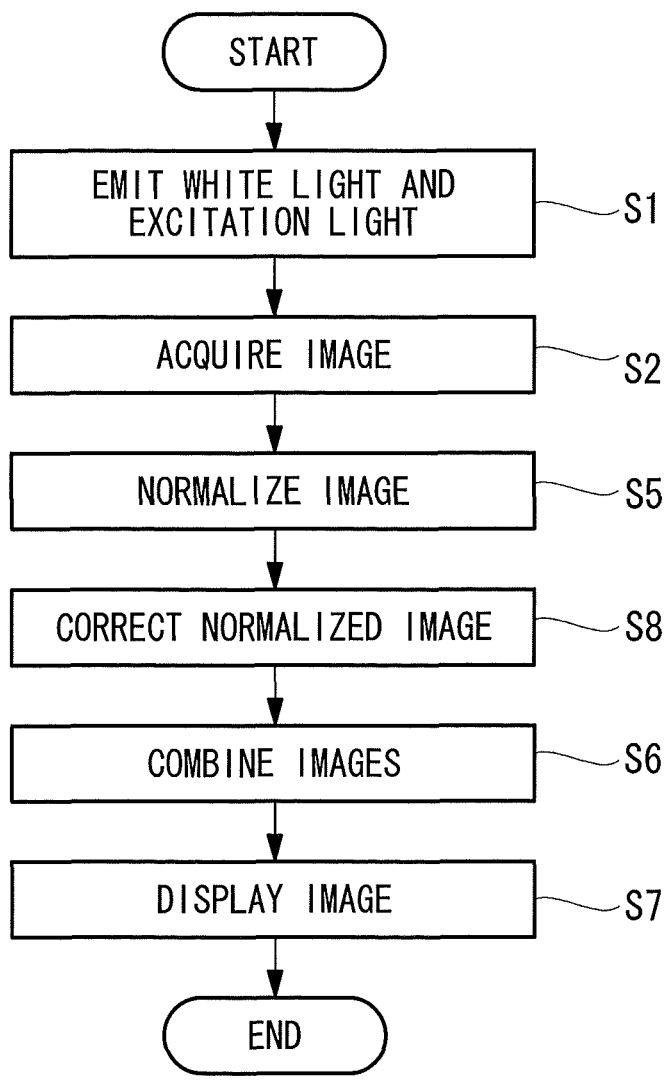
FIG. 7 is a flowchart showing a process of observing fluorescence from an object using the fluorescence observation apparatus in FIG. 6.

Furthermore, although the above-described embodiment is configured such that at least one of the fluorescence image and the white-light image is corrected by the correction coefficient, after which the fluorescence image is normalized by the corrected image, the image processing may be performed in the way shown in FIGS. 6 and 7 instead.

That is, the order of the image normalizing portion 22 and the image correcting portion 21 is exchanged: first, in the image normalizing portion 22, the fluorescence image $FL_{ij}$ generated by the fluorescence-image generating portion 19 is normalized by the white-light image $WL_{ij}$ generated by the white-light-image generating portion 20 (step S5), and then, the normalized fluorescence image $FL_{ij}/WL_{ij}$ is corrected by being multiplied by the correction coefficient W/F (step S8). In this way, it is possible to quickly acquire a normalized fluorescence image $FL'_{ij}/WL'_{ij}$ the same as above, with a small amount of calculation.

Furthermore, although the white-light image is employed as a return-light image used to normalize the fluorescence image in this embodiment, another arbitrary image acquired in the same irradiation area as the fluorescence image, such as an excitation-light image or an auto-fluorescence image, may be used instead.

Furthermore, although the image correcting portion 21 stores the correction coefficients, a storage unit (a light-distribution-characteristics-information storage unit; not shown) may be provided separately from the image correcting portion 21, and the image correcting portion 21 may perform image correction using correction coefficients stored in that storage unit.

Furthermore, although the image correcting portion 21 stores the correction coefficients, which are the ratios obtained by dividing the light distribution characteristics by the representative gradation values, instead of this, the light distribution characteristics themselves may be stored as the correction coefficients.

On the basis of the embodiment described above, the fluorescence image is normalized with high precision by using the fluorescence image and the return-light image, the fluorescence image and the return-light image being captured by cameras having different lens characteristics, enabling more quantitative fluorescence observation.

Furthermore, on the basis of the embodiment described above, the influence of the light distribution characteristics of the optical systems contained in the fluorescence image and return-light image used to normalize the fluorescence image is removed from those images. Thus, the influence due to the difference in light distribution characteristics is removed from the normalized fluorescence image, enabling more quantitative observation.

Furthermore, on the basis of the embodiment described above, the use of the light-distribution-characteristics ratio reduces the number of times the image correcting unit corrects the image, and makes it possible to remove the influence due to the difference in light distribution characteristics from the normalized fluorescence image, enabling more quantitative observation.

What is claimed is:

1. A fluorescence observation apparatus comprising:
    an illumination unit that irradiates an object with illumination light and excitation light;
    a fluorescence-image acquisition unit that captures an image of fluorescence generated by the object due to the object being irradiated with the excitation light from the illumination unit, thereby acquiring a fluorescence image;
    a return-light-image acquisition unit that captures an image of return light returning from the object due to the object being irradiated with the illumination light from the illumination unit, thereby acquiring a return-light image;
    a light-distribution-characteristics-information storage unit that stores information with regard to the light distribution characteristics of optical systems provided in the fluorescence-image acquisition unit and in the return-light-image acquisition unit;
    an image correcting unit that corrects at least one of the fluorescence image and the return-light image using the information with regard to the light distribution characteristics stored in the light-distribution-characteristics-information storage unit so that the light distribution characteristics contained in the fluorescence image and the return-light image are made equal to each other; and
    an image normalizing unit that normalizes the fluorescence image on the basis of the return-light image, each of the fluorescence image and the return-light image being corrected by the image correcting unit.

2. The fluorescence observation apparatus according to claim 1, wherein
    the light-distribution-characteristics-information storage unit stores, as the information with regard to the light distribution characteristics of the optical systems, the light distribution characteristics of the optical systems provided in the fluorescence-image acquisition unit and in the return-light-image acquisition unit, and
    the image correcting unit divides the fluorescence image by the light distribution characteristics of the optical system provided in the fluorescence-image acquisition unit and divides the return-light image by the light distribution characteristics of the optical system provided in the return-light-image acquisition unit.

3. The fluorescence observation apparatus according to claim 1, wherein
    the light-distribution-characteristics-information storage unit stores, as the information with regard to the light distribution characteristics of the optical systems, a light-distribution-characteristics ratio obtained by dividing the light distribution characteristics of the optical system provided in the fluorescence-image acquisition unit by the light distribution characteristics of the optical system provided in the return-light-image acquisition unit, and
    the image correcting unit divides the fluorescence image by the light-distribution-characteristics ratio.

4. The fluorescence observation apparatus according to claim 1, wherein
    the light-distribution-characteristics-information storage unit stores, as the information with regard to the light distribution characteristics of the optical systems, a light-distribution-characteristics ratio obtained by dividing the light distribution characteristics of the optical system provided in the return-light-image acquisition unit by the light distribution characteristics of the optical system provided in the fluorescence-image acquisition unit, and
    the image correcting unit divides the return-light image by the light-distribution-characteristics ratio.

5. A fluorescence observation apparatus comprising:
    an illumination unit that irradiates an object with illumination light and excitation light;
    a fluorescence-image acquisition unit that captures an image of fluorescence generated by the object due to the object being irradiated with the excitation light from the illumination unit, thereby acquiring a fluorescence image;
    a return-light-image acquisition unit that captures an image of return light returning from the object due to the object being irradiated with the illumination light from the illumination unit, thereby acquiring a return-light image;
    a light-distribution-characteristics-information storage unit that stores information with regard to the light distribution characteristics of optical systems provided in the fluorescence-image acquisition unit and in the return-light-image acquisition unit;
    an image normalizing unit that normalizes the fluorescence image acquired by the fluorescence-image acquisition unit by using the return-light image acquired by the return-light-image acquisition unit; and
    an image correcting unit that corrects the fluorescence image normalized by the image normalizing unit using the information with regard to the light distribution characteristics stored in the light-distribution-characteristics-information storage unit so that the light distribution characteristics contained in the fluorescence image and the return-light image are made equal to each other.

* * * * *